United States Patent
Hill (10) Patent No.: US 6,929,600 B2
(45) Date of Patent: Aug. 16, 2005

(54) APPARATUS FOR INTUBATION (76) Inventor: Stephen D. Hill, 223 Mineral Springs Road, RR.5, Huntsville, Ontario (CA), P1H 2N5

(*) Notice: Subject to any disclaimer, the term of this patent is extended or adjusted under 35 U.S.C. 154(b) by 163 days.

(21) Appl. No.: 10/199,707

(22) Filed: Jul. 23, 2002

(65) Prior Publication Data
US 2003/0078476 A1 Apr. 24, 2003

Related U.S. Application Data (60) Provisional application No. 60/307,134, filed on Jul. 24, 2001.

(51) Int. Cl.[7] .................................................. A61B 1/04
(52) U.S. Cl. ........................ 600/120; 600/160; 600/172
(58) Field of Search .............................. 600/109, 120, 600/160, 172–176, 117, 118

(56) References Cited

U.S. PATENT DOCUMENTS

| | | | |
|---|---|---|---|
| 3,257,902 A | 6/1966 | Hopkins | |
| 4,515,444 A | 5/1985 | Prescott et al. | |
| 4,608,966 A | 9/1986 | Storz | |
| 4,662,725 A | 5/1987 | Nisioka | |
| 4,723,843 A | 2/1988 | Zobel | |
| 4,742,819 A | * 5/1988 | George | 600/109 |
| 4,846,153 A | * 7/1989 | Berci | 600/109 |
| 5,168,864 A | 12/1992 | Shockey | |
| 5,183,031 A | 2/1993 | Rossoff | |
| 5,308,986 A | 5/1994 | Walker | |
| 5,363,838 A | * 11/1994 | George | 600/120 |
| 5,373,317 A | * 12/1994 | Salvati et al. | 348/65 |
| 5,415,158 A | 5/1995 | Barthel et al. | |
| 5,420,959 A | 5/1995 | Walker et al. | |
| 5,735,792 A | 4/1998 | Vanden Hoek et al. | |
| 5,827,178 A | * 10/1998 | Berall | 600/185 |
| 5,857,961 A | 1/1999 | Vanden Hoek et al. | |
| 5,879,289 A | * 3/1999 | Yarush et al. | 600/179 |
| 5,921,917 A | 7/1999 | Barthel et al. | |
| 5,941,816 A | 8/1999 | Barthel et al. | |
| 5,951,463 A | 9/1999 | Lombardi et al. | |
| 6,652,453 B2 | * 11/2003 | Smith et al. | 600/188 |
| 6,692,432 B1 | * 2/2004 | Yarush et al. | 600/179 |
| 2001/0001957 A1 | 5/2001 | Allgeyer | |
| 2003/0195390 A1 | * 10/2003 | Graumann | 600/188 |

OTHER PUBLICATIONS

Pages from www.keomed.com/shikani.htm "Clarus Medical Shikani Seeing Stylet".
Pages from www.clarus–medical.com/shikaniseeing-stylet.htm "The Shikani Seeing Stylet. Optimum Visualization and Illumination for Management of the Difficult Airway".
Pages from www.nanoptics.com/nanoscope.htm "The NanoScope™ An Intubation Imaging System".
www.leineroptics.com/etpage1.htm to www.leineroptics.com/etpage9.htm.
Pages from www.nanoptics.com/tutorial.htm "Fiberoptic Tutorial".
Pages from www.nanoptics.com/NanoscopePage.htm "Plastic Optical Fiber Endoscope: NANOSCOPE".

(Continued)

Primary Examiner—Beverly M. Flanagan
(74) Attorney, Agent, or Firm—Bereskin & Parr (57) ABSTRACT This invention relates to an apparatus which is used in conjunction with an endotracheal tube to provide visual information during intubation. The visual information is used by a medical practitioner in order to successfully insert and position the endotracheal tube into the trachea of a patient who is being intubated.

19 Claims, 4 Drawing Sheets

OTHER PUBLICATIONS

Pages from www.asancep.org.uk/Endotrachealtubeintroducer.htm. The ASA—The Ambulance Service Association National Clinical Effectiveness Programme. Difficult intubation protocol: use of the endotracheal tube introducer (gum–elastic bougie), Woollard, M., Pitt, K. Intenal Document. Welsh Ambulance Services NHS Trust.

Pages from www.frca.co.uk/printfriendly.aspx?articleid=244. Anaesthesia UK. The Portex Endotracheal Tube Intoducer (bougie).

Pages from www.vitaid.ca/usa/glidescope–index.php. Vitaid Airway Management—Glidescope.

The GlideScope Video Intubation System—Operator & Service Manual, 2003, pp. 1–19.

* cited by examiner

APPARATUS FOR INTUBATION

FIELD OF THE INVENTION

The invention relates to an apparatus for providing visual information during the ventilation of an individual. More particularly, this invention relates to an apparatus for use in conjunction with an endotracheal tube to provide ventilation for an individual.

BACKGROUND OF THE INVENTION

Endotracheal intubation is a common technique that is used when an individual (hereafter referred to as the patient) must be ventilated such as after receiving a general anesthetic. The technique consists of placing an endotracheal tube (i.e. a flexible, plastic tube) into the patient's trachea to ventilate his/her lungs. During intubation, the endotracheal tube must be inserted past the patient's teeth and tongue and then past the epiglottis and the vocal cords into the trachea. The endotracheal tube should be placed about 1 to 2 inches before the bifurcation of the trachea in order to ventilate both of the patient's lungs equally.

An anestheologist, ER physician, RT, paramedic or any other suitable medical practitioner, passes the endotracheal tube into the trachea with the aid of a laryngoscope that is introduced into the patient's mouth and upper airway. The laryngoscope consists of a blade of varying size, a fiberoptic light source and a handle that contains the power source for the light. The blade of the laryngoscope, which is curved for adults, is used to move the patient's epiglottis to expose the underlying glottis (the epiglottis and glottis form a valve-like structure which provides an opening to the trachea). An opening is then formed through which two white vocal cords are seen. The tip of the endotracheal tube is then advanced through the vocal cords. At this point, the endotracheal tube is secured and a pressure cuff, on the outside of the endotracheal tube, is inflated so that the endotracheal tube pushes against the inner lining of the trachea. This is done to provide a clear airway for the patient and to prevent the aspiration of blood, mucus and gastric acid which is important since these materials may cause pneumonitis or bronchial obstruction. The endotracheal tube is then secured such that it is held tightly in place and not allowed to slide up and down the patient's trachea.

In certain cases, the epiglottis and glottis valve-like structure, as well as the vocal cords, form what is known as a "difficult airway". This difficult airway presents a challenge to the medical practitioner who is performing the intubation. The difficult airway is particularly troublesome in the case of blind intubation, in which the vocal cords are not directly visible with a conventional laryngoscope. This problem may be compounded by patients who have, for example, a short muscular neck with a full set of teeth, a receding lower jaw or temporo-mandibular disease. As a result it is likely that the intubation process will fail. Since 1992, failed intubations have resulted in one third of all anesthesia related deaths during operation procedures. In addition, failed intubation may also lead to bleeding, swelling, laryngospasm, discomfort and hoarseness. Therefore, professionals in the field of anesthesiology are interested in improving the intubation process.

In response, many devices have been developed that are used to gain "blind" access to the trachea. Currently, there is a surge of interest in flexible fiberoptics that are used, either alone or in conjunction with endotracheal tubes, to perform intubation. However, scopes employing flexible fiberoptics are costly and employ a display means, such as an eyepiece or a remote screen display, that is awkward to use during the intubation process. The high costs result in limited access to these devices which consequently leads to a lack of user skill for these types of scopes. This makes the use of these fiberoptic scopes both time consuming and cumbersome which is troublesome for situations in which the medical personnel must act quickly.

SUMMARY OF THE INVENTION

This invention relates to a vision system that is used in conjunction with an endotracheal tube to provide visual information during intubation. The visual information is related to objects that are not accessible by direct viewing. The visual information is used by a medical practitioner to successfully insert the endotracheal tube within the trachea of the individual being intubated.

The vision system is a video scope comprising an integrated monitor that is mounted on a stylet such that the monitor is facing towards the medical practitioner. The integrated monitor provides the medical practitioner with an improved view of the patient's airway and increased flexibility (i.e. the monitor can be viewed from a distance) in comparison with vision systems that use an eyepiece. The stylet is inserted into the endotracheal tube to form a single medical instrument that feels similar in use to the combination of a laryngoscope, a stylet and an endotracheal tube that is conventionally used to intubate a patient. Accordingly, a medical practitioner should find it easy to adapt to and use the vision system of the present invention.

In a first aspect, the invention provides a vision system for obtaining an image of an inner cavity. The vision system has a stylet with a first end, a second end and a flexible shaft disposed therebetween. The first end of the stylet is placed within the cavity during use and the shaft has a lumen. The vision system further has a module that is mounted adjacent to the second end of the stylet. The module has a monitor upon which the image is displayed. The vision system also has an optical system disposed within the module and the lumen for providing light to illuminate a region proximal to the first end of the stylet and for obtaining an image of the illuminated region for displaying on the monitor.

In an alternative embodiment, the invention provides a vision system for obtaining an image of an inner cavity. The vision system includes a stylet having a first end, a second end and a flexible shaft disposed therebetween. The first end is placed within the cavity during use and the shaft has a lumen. The vision system further includes an optical system that is disposed within the lumen for providing light to illuminate a region proximal to the first end of the stylet and for obtaining an image of the illuminated region for displaying on a monitor. The vision system further includes an extension piece that is releasably connectable to the second end of the stylet to increase the length of the stylet.

In yet another alternative embodiment, the invention provides a vision system for obtaining an image of an inner cavity. The vision system includes a stylet having a first end, a second end and a flexible shaft disposed therebetween. The first end is placed within the cavity during use and the shaft has a lumen. The vision system further includes a module, mounted adjacent to the second end of the stylet, having a monitor upon which the image is displayed. The vision system also includes an optical system that is disposed within the module and the lumen. The optical system provides light to illuminate a region proximal to the first end of the stylet and obtains an image of the illuminated region for displaying on the monitor. The second end of the stylet is flexible thereby permitting adjustment of the position of the monitor.

BRIEF DESCRIPTION OF THE DRAWINGS

For a better understanding of the present invention and to show more clearly how it may be carried into effect, reference will now be made, by way of example, to the accompanying drawings which show preferred embodiments of the present invention and in which:

FIG. 2b is an end view of the tip of the video scope of FIG. 2a;

FIG. 2c is a schematic diagram of the optical system used by the video scope of FIG. 2a;

FIG. 2d is a schematic diagram of an alternative embodiment of the optical system used by the video scope of FIG. 2a;

FIG. 4a is a partial front view of an alternative embodiment of the video scope of FIG. 2a;

FIG. 4b is a front view of another alternative embodiment of the video scope of FIG. 2a;

FIG. 5b is an enlarged view of the tip of the video scope shown in FIG. 5a;

DETAILED DESCRIPTION OF THE INVENTION

The subject invention comprises a video scope, otherwise known as a "seeing eye stylet", that is used in conjunction with an endotracheal tube during intubation. A conventional endotracheal tube will first be described. Several embodiments of the video scope will then be described followed by a description of several methods of use for the video scope.

Figure 1:
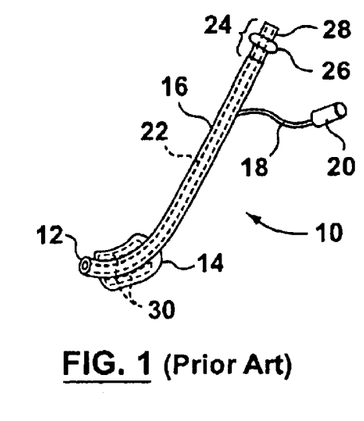
FIG. 1 is a perspective view of an endotracheal tube in accordance with the prior art.

Referring to FIG. 1, shown therein is an endotracheal tube 10 which is used to intubate a patient. The endotracheal tube 10 comprises a first end (i.e. a tip) 12, a cuff 14, a shaft 16, a tube 18, a nozzle 20, a lumen 22 and a universal adaptor 24 having a lip piece 26 and a second end 28. The lumen 22 is a hollow passageway that allows for the transfer of air to and from the patient's lungs. The tip 12 of the endotracheal tube 10 is inserted into the patient and the universal adaptor 24 is connected to a machine, such as a ventilator, which provides air to the patient's lungs.

The tube 18 is connected to the cuff 14 to provide for inflation and deflation of the cuff 14. The nozzle 20 is used to connect the tube 18 to an inflation device (not shown). Accordingly, the cuff 14 has internal chambers 30 which inflate while receiving air from the tube 18. The cuff 14 is inflated until the exterior of the cuff 14 touches the interior of the patient's trachea. Conversely, the internal chambers 30 deliver air to the tube 18 while deflating. Alternatively, another suitable gas such as oxygen and the like or a liquid may be used in place of air to inflate the chambers 30. Furthermore, the endotracheal tube 10 may alternatively have a pilot balloon (not shown) that is located under the nozzle 20. The pilot balloon is repeatedly squeezed to provide air to the cuff 14.

The endotracheal tube 10 may be made from separate pieces of flexible plastic that are molded and connected into the shape shown in FIG. 1. Typical lengths for the shaft 16 of the endotracheal tube 10 are approximately 19 to 20 cm for women and 21 to 23 cm for men. In both cases, the entire length of the endotracheal tube 10 may be approximately 30 cm. The internal diameter of the endotracheal tube 10 (i.e. the diameter of the lumen 22) is approximately 7.5 mm for women and 8 to 8.5 mm for men. For children, the endotracheal tube 10 does not have the cuff 14, the tube 18 and the nozzle 20.

Reference is next made to FIGS. 2a to 2d which show a video scope 40 in accordance with the present invention. The video scope 40 is ideally designed for use with the endotracheal tube 10 but may also be used for other applications. The video scope 40 comprises a stylet 42, a module 44 and an optical system 46 that is disposed within the stylet 42 and the module 44. The stylet 42 may be connected with the module 44 in several ways as described further below. The stylet 42 comprises a first end 48, a shaft 50, a connector 52 operably connected to the shaft 50 and a second end 54. The shaft 50 also has an inner lumen (not shown) that extends throughout the length of the shaft 50 for housing a portion of the optical system 46 as well as an optional channel as described further below. The module 44 comprises a monitor 56, a power button 58, a power source 60, a portion of the optical system 46 and related circuitry (not shown) that is required for the operation of the video scope 40.

Figure 2A:
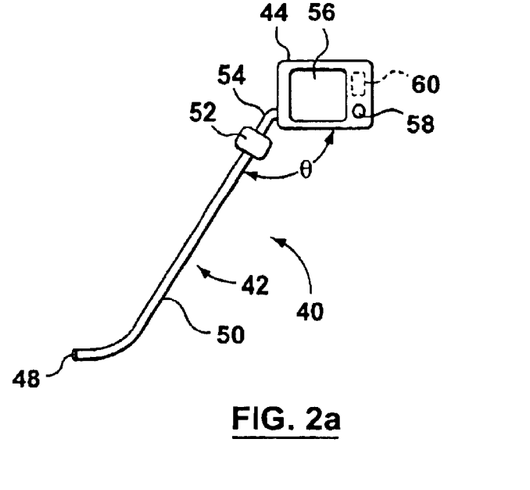
FIG. 2a is a front view of a video scope in accordance with the present invention.
Figure 2B:
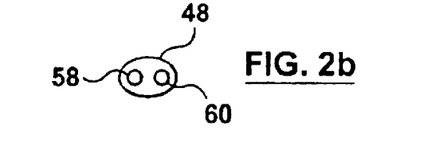

The monitor 56 provides for a more natural intubation procedure since the medical practitioner is looking in the direction of the monitor 56 which is also in the working direction of the endotracheal tube 10 (i.e. the same direction that the medical practitioner would be facing if he/she was performing conventional intubation). This is to be contrasted with other vision systems in which the medical personnel must look at a remote video screen or through an eyepiece during the intubation process. Looking at a remote video screen may force the medical practitioner to twist his/her body to look in one direction while performing the intubation in a different direction. This can be cumbersome and disorienting. In addition, looking through an eyepiece while intubating a patient can be quite awkward since the medical practitioner may have to bend over the patient's body to get close to the body for intubation while also maintaining contact with the eyepiece. The integrated monitor 56 provides a better image of the patient's airway in comparison to a video system that uses an eyepiece. Furthermore, the use of an integrated monitor 56 provides for a self-contained vision system that can be used out in the field rather than solely in a hospital room since the video scope 40 does not need to be connected with any other electronic medical equipment in order to function.

Figure 2C:
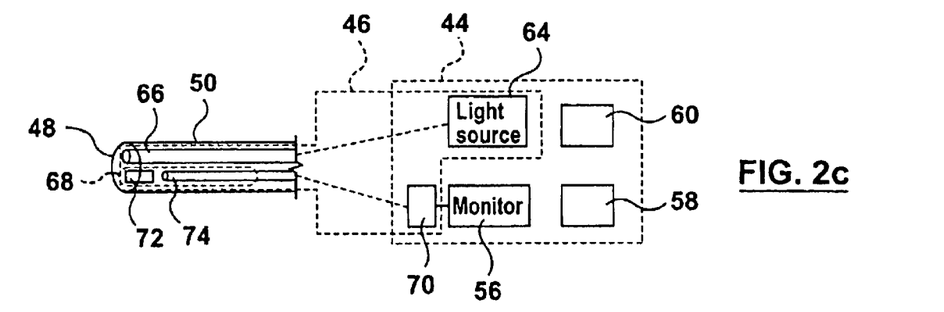

The optical system 46 of the video scope 40 comprises a light source 64 that is disposed within the module 44, an illumination channel 66 in communication with the light source 64, and an image channel 68. The light source 64 may be a light emitting diode for example. Both the illumination channel 66 and the image channel 68 are disposed within the lumen of the shaft 50 and extend substantially throughout the entire length of the shaft 50. The optical system 46 further comprises a light sensor 70 such as a camera chip that is disposed within the module 44 and in communication with the image channel 68. Each component of the optical system 46 is preferably mounted in place by using transparent optical cement or epoxy. The optical system 46 may optionally have a lens irrigation capability for self-cleaning purposes.

The illumination channel 66 comprises an incoherent fiber bundle having a first plurality of optical fibers that are designed to maximize light-carrying capacity. Accordingly, the number of optical fibers in the illumination channel 66 and the width of these fibers are selected to provide adequate light intensity to illuminate the region in front of the tip 48 of the stylet 42. The image channel 68 comprises an objective lens system 72 in optical communication with an image guide 74 that is connected to the light sensor 70. The objective lens system 72 creates an image of the region that is directly in front of the tip 48 of the stylet 42 when the region is being illuminated by the illumination channel 66. The image guide 74 must be placed at the location of the created image so that the image is transmitted to the light sensor 70. This location corresponds to the focal length of the objective lens system 72 which depends on its numerical aperture. The stylet 42 is placed in the endotracheal tube 10 such that the end of the illumination channel 66 is substantially coterminous with the end of the endotracheal tube 10. This allows the video scope 40 to provide an image of the airway directly in front of the endotracheal tube 10 as well as being atraumatic (to reduce the possibility of damaging the patient's airway). Furthermore, the end of the illumination channel 66 and the end of the image channel 68 are also preferably coterminous.

The image guide 74 is a coherent fiber bundle comprising a second plurality of optical fibers that are preferably thin to provide as high an image resolution as possible. The second plurality of fibers must be oriented in the same fashion at both ends of the image guide 74 in order to properly transmit the image to the light sensor 70. Accordingly, the second plurality of fibers only need to be fixed in place at the ends of the image guide 74 so that most of the length image guide 74 may be flexed to allow for different shapes for the stylet 42 and the endotracheal tube 10.

The optical fibers of the illumination channel 60 and the image channel 62 should be chosen to have adequate quality, mechanical strength and flexibility. Glass optical fibers are intrinsically brittle, and when broken, create darkened areas in the image viewed on the monitor 56. Plastic optical fibers are more flexible than glass optical fibers, however, glass optical fibers provide a brighter image for viewing on the monitor 56. Accordingly, either glass or plastic optical fibers may be used depending on whether increased flexibility or a brighter image is desirable. In either case, the optical fibers are preferably encased in a flexible jacket of thin-wall plastic for protection.

The light sensor 70 may be either a CCD or a CMOS camera chip. These camera chips consist of light detecting sites or photosites arranged in a grid pattern which record images of the light patterns that shine on their surface. Hence, the resolution of these camera chips is related to the number of pixels in the array as well as the imaging optics of the remainder of the optical system 46. A CMOS camera chip may be preferable to a CCD camera chip since, in general, CMOS camera chips have low power consumption, can provide a direct digital output and are small in size. However, some CMOS camera chips will provide an analog output signal that is encoded in a video format such as PAL, NTSC, S-video, etc. Accordingly, a video capture card must be used with such CMOS camera chips to provide analog to digital conversion. Alternatively, other CMOS camera chips have digital outputs consisting of a 4, 8 or 16 bit data bus.

Figure 2D:
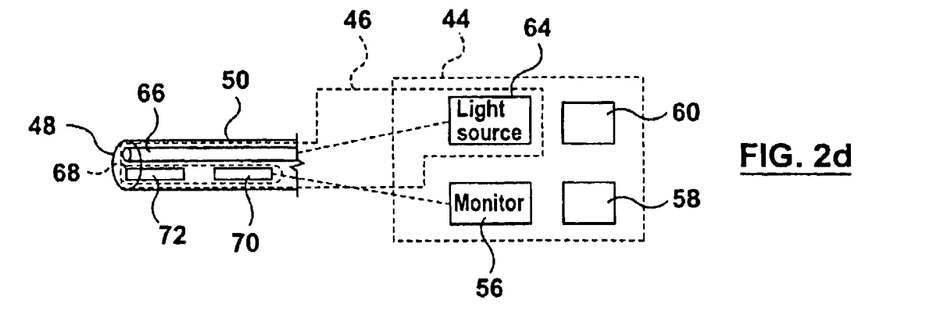

Referring now to FIG. 2d, shown therein is an alternative embodiment of an optical system 46a in which there are two modifications. The light sensor 70 is now positioned at the tip 48 of the stylet 42 rather than in the module 44 so that there is no need for the image guide 74. The light sensor 70 is placed at the focal point of the objective lens system 72 in order to sense the reflected light from the region directly in front of the tip 48 of the stylet 42. The light sensor 70 is connected with the monitor 52 via a data bus that facilitates the transmission of an appropriate number of data bits (this depends on the type of camera chip that is used). Since the optical system 46a does not rely on an image guide, images with dark areas that are due to broken optical fibers should not be experienced.

The video scope 40 may optionally have a third channel (not shown) in the lumen of the shaft 50 which has an opening at the tip 48 of the stylet 42 and provides a suction or irrigation capability. Accordingly, the third channel may be connected to a side port located at the module 44 that is coupled with suction or irrigation tubing thereat. The third channel may be used to suction secretions in the oral and tracheal cavities that may be obstructing the view of the medical practitioner performing the intubation. Alternatively, in the case of irrigation, the third channel may be used to "clean" the area directly in front of the tip 48 of the stylet 42, using saline solution, for example, to provide a better image on the monitor 56. Alternatively, the third channel may be used to clean portions of the stylet 42. The inclusion of the third channel may warrant a larger diameter for the shaft 50.

The majority of the shaft 50 of the stylet 42 may be made from a semi-rigid material such as aluminum, a flexible metal, a medical-grade plastic or a polymer. A plastic wrap may also be placed on the exterior of the stylet 42. The stylet 42 is made from a semi-rigid material so that the stylet 42 may be shaped into a gentle curve or an L-shaped configuration to accommodate the patient being intubated. The shaft 50 may preferably have a French diameter of 14 or 16 (i.e. a diameter of approximately 5 or 7 mm). Since the video scope 40 is designed for use with the endotracheal tube 10, the shaft 50 is shaped and dimensioned to fit inside the endotracheal tube 10. In addition, the shaft 50 may be covered with a soft clear coating to protect the shaft 50 during sterilization. The coating may also protect the shaft 50 from any water-soluble lubricants that may be used to allow for easy insertion and removal of the stylet 42 into and out of the endotracheal tube 10. The coating on the exterior of the shaft 50 may also be used to prevent trauma to the trachea caused by contact with the tip 48 of the stylet 42. Furthermore, the tip 48 of the stylet 42 may have a shape that is slightly more bulbous than the remainder of the stylet 42 so as to reduce the possibility of damaging the patient's airway during intubation.

The shaft 50 may be rigidly attached to the module 44 to provide increased stability for the video scope 40. In addition, the connector 52 may be slidably mounted on the shaft 48 such that the "effective" length of the shaft 50 is adjustable. The connector 52 may be slid upwards along the shaft 50 to make the shaft 50 longer or the connector 52 may be slid downwards along the shaft 50 to make the shaft 50 shorter. The variable length property of the shaft 50 allows the video scope 40 to be used with a variety of endotracheal tubes of varying lengths so that the video scope 40 may be used on a variety of patients ranging from infants, to adolescents and adults.

In an alternative embodiment, the module 44 may be rotatably mounted onto the shaft 50 via a rotating connector (not shown) at the second end 54 of the shaft 48. Alternatively, the portion of the shaft 50 near the second end 54 may be made flexible to allow the angle θ (see FIG. 2*a*) between the module 44 and the shaft 50 to be increased (decreased) so that the monitor 56 rotates upwards (downwards) about a horizontal axis. The flexibility of the second end 54 of the shaft 50 may also allow for rotation of the module 44 about a vertical axis so that the medical practitioner may further adjust the orientation of the monitor 56. These two alternatives may be included in the same embodiment of the video scope 40. The flexibility of the second end 54 may be achieved by making the shaft 48 of the stylet 42 more flexible in the region proximal to the second end 54 compared to the remainder of the stylet 42. Alternatively, a pivot means such as a ball joint may be connected to the second end 54. In this case, there would be a hole to allow for the passage of the optical fibers between the shaft 48 and the module 44. These features make it easier for a medical practitioner to use the video scope 40 during intubation. In particular, the medical practitioner could adjust the orientation of the monitor 56 during intubation so that the medical practitioner does not have to stretch or twist his/her neck to look at an image of the trachea during intubation (as would be the case if a remote video screen or an eyepiece were used).

The monitor 56 on the module 44 is preferably an LCD screen having small dimensions. An exemplary size of the monitor 56 may be 6 cm in length and 4 cm in height or smaller. Accordingly, the monitor 56 provides an image that is larger than that obtained with eyepieces of prior art vision systems. Therefore, the medical practitioner may view the monitor 56 without having to place his/her eye adjacent to the module 44 as in the case for an eyepiece. Digital imaging technology may also be incorporated into the module 44 to enhance the images seen on the monitor 56 and to save these images. The saved images may be used for later reference to confirm proper placement of the endotracheal tube 10, for medical or legal purposes, or to provide images of the airway where there may be a lesion or other medical pathology. Accordingly, there may be a port (not shown) on the module 44 that is used to transfer the saved images to another computing device.

The power button 58 is used to turn the video scope 40 on and off. The power button 58 may be a pressure sensitive switch or an on/off toggle switch. The video scope 40 may also have an automatic "delay off" feature so that the video scope 40 is turned off after a certain duration of inactivity. The duration of inactivity may be monitored via an internal timer. This feature would be used to conserve the energy of the power source 60 in case the video scope 40 is inadvertently left on.

The power source 60 provides power to the electrical components of the video scope 40 and may preferably be a battery, but may alternately be a connection to an external power source such as an electric wire and plug for connection to a standard 120 Volt AC source. If batteries are used for the power source 60, a "Low Battery" indicator may be displayed on the monitor 56 to indicate to the medical practitioner that the voltage level of the batteries is low.

The video scope 40 may also have a timer connected to a sound alarm (both not shown) that are both disposed within the module 44. The timer records the amount of time that has elapsed during the intubation process. If the elapsed time is greater than a predetermined amount of time that corresponds to a safe intubation, then a timer will trigger the alarm to sound. This indicates to the medical practitioner that the patient must be reoxygenated in order to prevent anoxia from occurring. Alternatively, a visual alarm may be used in which a visual message is displayed on the monitor 56. In a further alternative, both a sound and visual alarm may be used to alert the medical practitioner.

Figure 3:
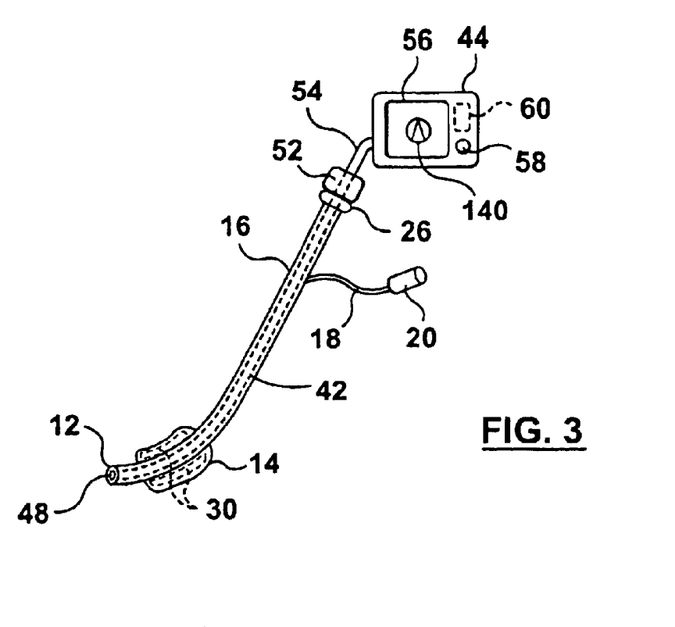
FIG. 3 is an isometric view of the video scope of FIG. 2a inserted into an endotracheal tube.

To use the video scope 40 in conjunction with the endotracheal tube 10, the tip 48 of the stylet 42 is slid into the second end 28 of the endotracheal tube 10. The stylet 42 is inserted into the endotracheal tube 10 until the tip 48 of the stylet 42 lies approximately flush with the tip 12 of the endotracheal tube 10. This is done so that the tip 48 of the stylet 42 does not cause any trauma to the patient's airway when the stylet 42 is inserted into the patient. A tip 48 which is more bulbous may also be used for this reason. The connector 52 fits snugly over the universal adaptor 24 and lies against the lip piece 26 of the endotracheal tube 10 to securely fasten the stylet 42 thereto in a friction-fit fashion. This prevents rotation of the stylet 42 or disengagement from the endotracheal tube 10. This also allows the video scope 40 and the endotracheal tube 10 to form a single piece of medical equipment. Alternatively, rather than utilizing a friction-fit connection, the connector 52 may utilize a fastener (not shown) that secures the connector 52 to the universal adaptor 24. The fastener may comprise a set-screw, for example, which is rotated such that the bottom of the set-screw engages the outer surface of the universal adaptor 24. Alternatively, the fastener may be a member having a cam-shaft surface that is rotated to engage the underside of the lip piece 26. The combination of the video scope 40 and the endotracheal tube 10 is depicted in FIG. 3.

As previously mentioned, the connector 52 may also be slidably mounted on the shaft 50 of the stylet 42 so that the position of the connector 52 may be adjusted to accommodate endotracheal tubes of varying lengths. Any of the mechanisms described above may be used to secure the connector 52 to the universal adaptor 24. Furthermore, the portion of the shaft 50 of the stylet 42 over which the connector 52 slides is preferably more rigid than the remainder of the stylet 42 so that the connector 52 can easily slide there along. The increased rigidity of the stylet 42 in this area will also make it easier for a medical practitioner to attach and de-attach the module 44 from the stylet 42 as described below. The position of the connector 52 may also be adjusted so that the tip 48 of the stylet 42 extends approximately 1 to 2 cm beyond the tip 12 of the endotracheal tube 10 to allow the tip 48 to be used to gain access to more confined regions of the patient's airway.

Figure 4A:
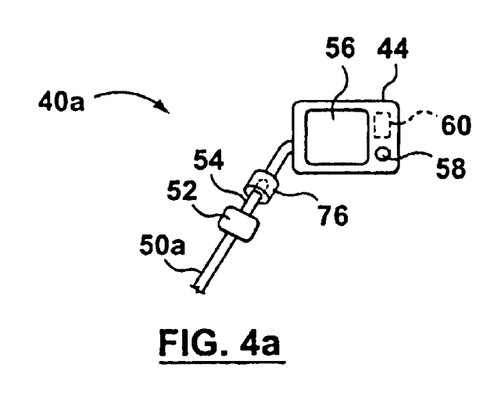

Referring now to FIG. 4*a*, shown therein is a partial view of an alternative embodiment of a video scope 40*a*, in which the module 44 may be releasably mounted to a shaft 50*a* having a male connector at the second end 54. The video scope 40*a* has every component of the video scope 40 except for the addition of a connector 76 which slidably, releasably mounts onto the male connector at the second end 54 of the shaft 50*a*. This detachable feature allows the module 44 to be detached from the shaft 50*a* of the stylet 42 so that the shaft 50*a* may be disinfected for use with different patients. Furthermore, this feature allows the module 44 to be releasably attached to stylets having differing lengths and diameters.

Figure 4B:
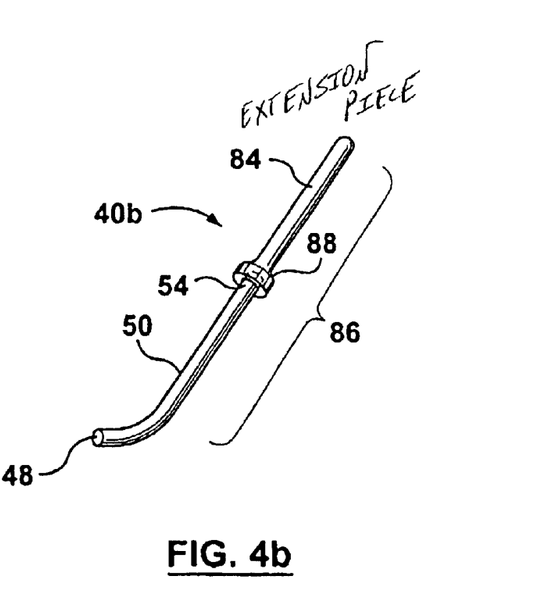

Referring now to FIG. 4*b*, shown therein is a front view of another alternative embodiment of the video scope 40*b* having an extension piece 84 that may be used to provide an extended stylet 86. The extension piece 84 has a female connector 88 that releasably, slidably engages the second end 54 of the shaft 50b. The extended stylet 86 may be used to employ a "railroading" intubation technique in which the video scope 40b is placed into the patient's trachea without first placing the video scope 40b into an endotracheal tube. This may be necessary if the patient has a particularly small airway in which case it would be easier to insert the stylet 42 without the larger bulky endotracheal tube. The module 44 may then be removed such that only the stylet 42 remains in the patient's trachea. The extension piece 84 may then be attached to the stylet 42 to provide the extended stylet 86. An endotracheal tube 10 may then be inserted over the extension piece 84 and slid down the extended stylet 86 until the endotracheal tube 10 was in the proper position within the patient's trachea (to facilitate this, the connector 52 has been removed). The endotracheal tube 10 would then be fastened in place and the extended stylet 86 removed.

Figure 5A:
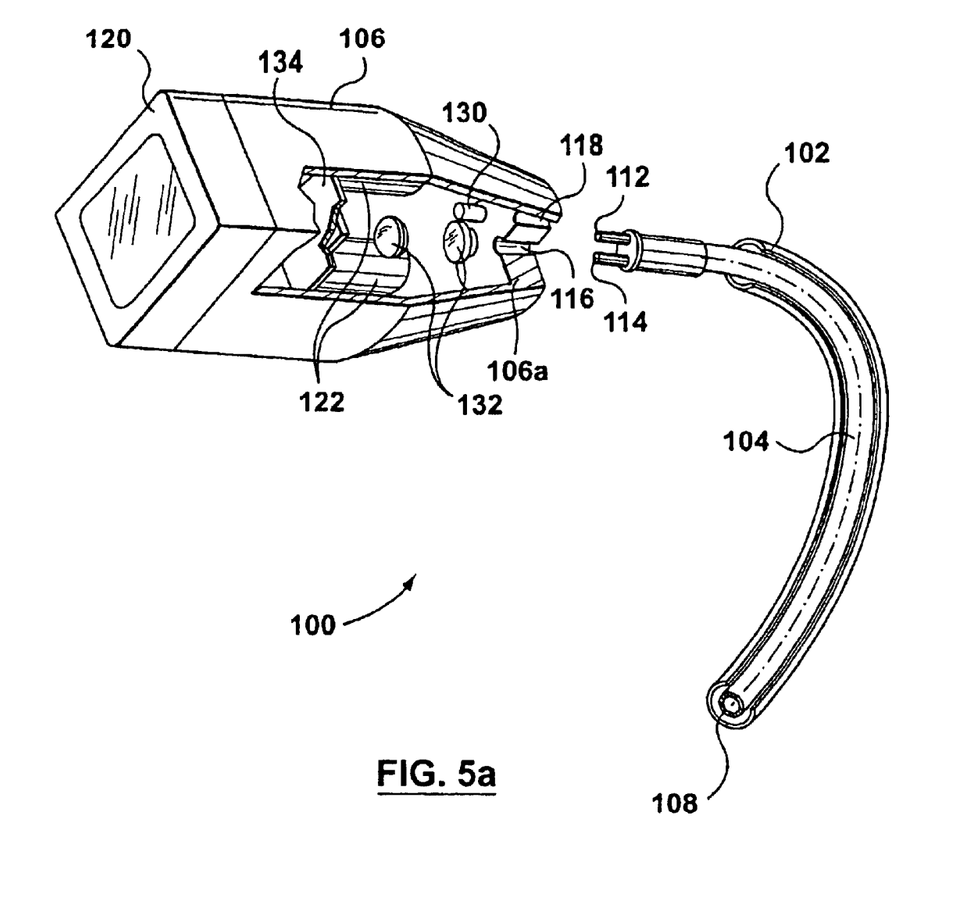
FIG. 5a is an isometric view of another alternative embodiment of a video scope in accordance with the present invention.
Figure 5B:
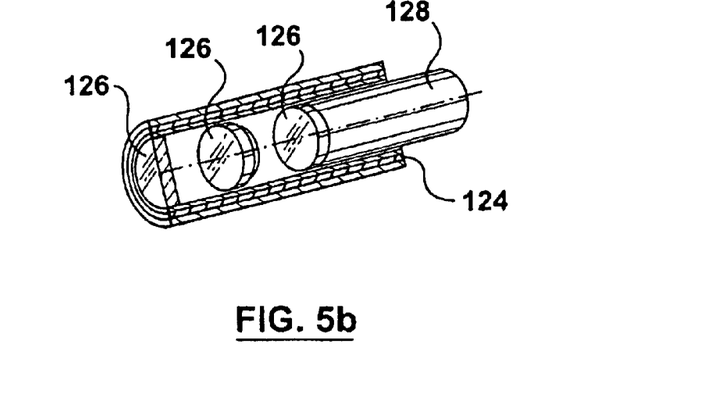

Referring now to FIGS. 5a and 5b, shown therein is an alternative embodiment of a video scope 100 that is inserted within a simplified endotracheal tube 102. The video scope 100 comprises a stylet 104 that is releasably connectable to a module 106. The stylet 104 has a lumen (not shown), a first end 108 and a second end 110 upon which two prongs 112 and 114 are mounted. The prongs 112 and 114 releasably slidably engage two channels 116 and 118 on the front portion 106a of the module 106. Accordingly, the stylet 104 may be disengaged from the module 106 to allow the stylet 104 to be cleaned as well as to allow the railroading intubation technique to be performed. The stylet 104 is made from semi-rigid material to allow for flexibility in shaping the stylet 104 for ease of visualization of the larynx and trachea as well as for placement of the endotracheal tube 102 within the patient. The diameter of the stylet 104 is determined in part by the components that are housed inside the stylet 104. The stylet 104 also preferably has a rigid portion so that a medical practitioner may grip this portion to attach and detach the module 106 from the stylet 104. The stylet 104 is also self-contained so that it may be used out in the field rather than solely in a medical room setting.

The module 106 comprises a monitor 120 upon which is displayed an image of the region in front of the tip 108 of the stylet 104. The monitor 120 is preferably an LCD screen having a small size but preferably larger than the eyepieces used with prior art vision systems. The module 106 further comprises a power source 122, a power button (not shown) as well as the electronics required for the proper functioning of the video scope 100. The power source 122 is preferably a pair of rechargeable batteries as shown.

The video scope 100 also comprises an optical system that is housed within the lumen of the stylet 104 and the module 106. The optical system comprises illumination fiber optics 124, an objective lens system 126 and a flexible image guide 128 that are housed within the lumen of the stylet 104. The illumination fiber optics 124 are disposed annularly about the circumference of the flexible image guide 128. The illumination fiber optics 124 and the image guide 128 comprise appropriate optical fibers as discussed previously. Furthermore, the illumination fiber optics 124 are preferably coterminous with the flexible image guide 128 at the tip 108 of the stylet 104. The optical system further comprises a light source 130, a set of relay lenses 132 and a light sensor 134 which are mounted within the module 106. The light source 130 may be a light emitting diode and the light sensor 134 may be a CCD or CMOS camera chip as previously discussed. Alternatively, the light sensor 134 may be disposed within the lumen of the stylet 104 to receive the image that is obtained by the objective lens system 126. The image guide 128 would not be needed in this case.

The prongs 112 and 114 are made of appropriate fiber optic material encased within a suitable plastic or metal for protection and rigidity. The prongs 112 and 114 are connected to the illumination fiber optics 124 and the flexible image guide 128 respectively. The prongs 112 and 114 provide an optical coupling between the components of the optical system that are housed in the stylet 104 and the components of the optical system that are housed in the module 106. Accordingly the prongs provide a mechanical and optical coupling between the stylet 104 and the module 106.

Figure 5C:
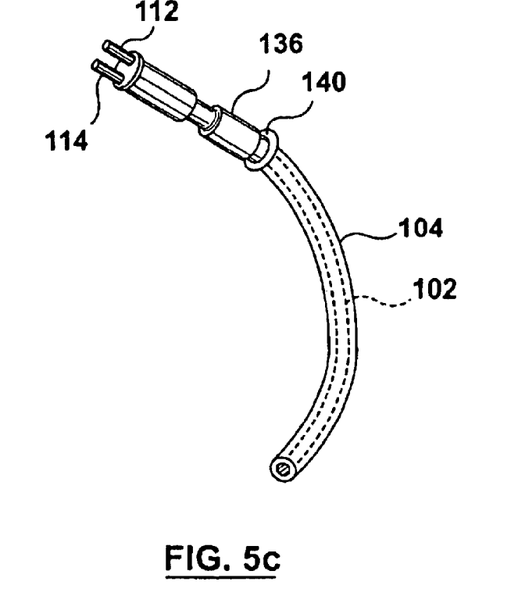
FIG. 5c is a partial front view illustrating the connectivity between the video scope of FIG. 5a and an endotracheal tube.

The stylet 104 may further have a connector 136 (see FIG. 5c) which is slidably mounted on the stylet 104. Accordingly, the connector 136 may be slid up and down the stylet 104 to provide connection to the universal adaptor 140 for a variety of endotracheal tubes having various lengths. The connector 136 is preferably dimensioned to make a secure, friction fit with the universal adaptor 140. Alternatively, the other connection mechanisms described previously may be employed to connect the connector 136 with the universal adaptor 24 of the endotracheal tube 10. The stylet 104 may further contain a third channel within the lumen for providing a suction or irrigation capability as previously described for the video scope 40.

In use, the light source 130 generates light that is transmitted by prong 112 to the illumination fiber optics 124 to illuminate the region directly in front of the tip 108 of the stylet 104. Light is reflected from the portion of the airway that is directly in front of the stylet 104. The reflected light is then collected by the objective lens system 126 and transmitted to the flexible image guide 128. The prong 114 receives the light that is transmitted along the flexible image guide 128 and transmits this light to the set of relay lenses 132 which project the light onto the light sensor 134. The image represented by the transmitted light that is sensed by the light sensor 134 is then displayed on the monitor 120. As discussed previously, depending on the type of camera chip used, a real-time video feed may be obtained for display on the monitor 120. The lenses of the optical system described in FIGS. 5a and 5b are preferably fixed in place with transparent optical cement.

Figure 6A:
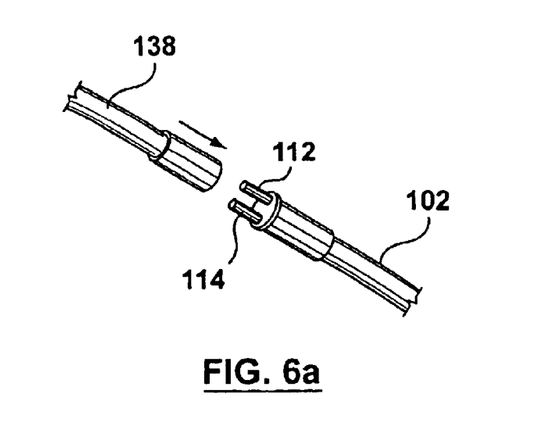
FIG. 6a is a partial front view of an alternative embodiment of the video scope of FIG. 5a having an extension piece; and, FIG. 6b is a front view of another alternative embodiment of the video scope of FIG. 5a having an angled stylet.
Figure 6B:
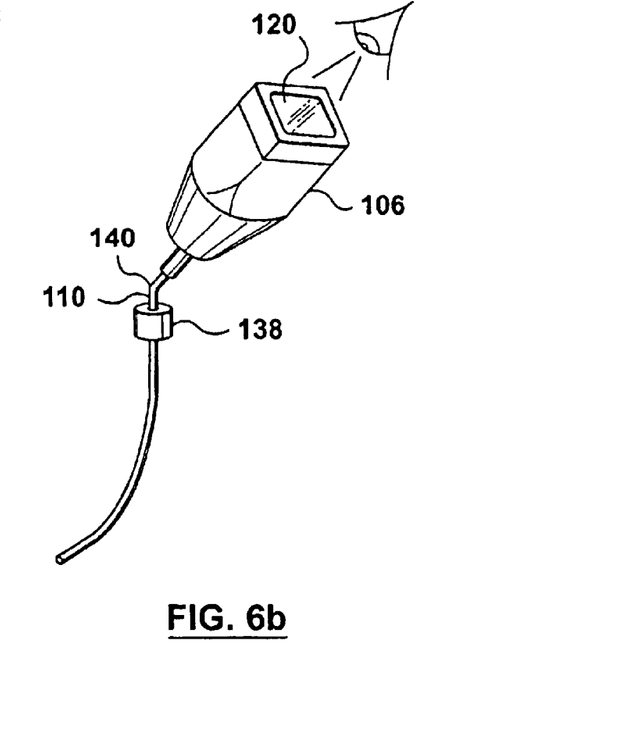

Referring now to FIGS. 6a and 6b, a number of similar modifications can be made to the video scope 100 as was already described for the video scope 40. For instance, the stylet 104 is adapted to releasably engage an extension piece 136 (i.e. see FIG. 6a). This would allow the railroading intubation technique to be used on the patient as previously described. Alternatively, or in combination with the alternative embodiment just discussed, the stylet 104 may either have a predetermined angled bend 140 at the second end 110 or be flexible in this area to allow a medical practitioner to create a desired bend to manipulate the orientation of the module 106 (see FIG. 6b). The angled bend 140 may preferably be such that the monitor 120 is directly in line with the eyes of the medical practitioner. As mentioned previously, the angled bend 140 would allow the medical practitioner greater flexibility in using the video scope 100 since the line of sight of the monitor 120 can be adjusted to accommodate the working environment. Alternatively, rather than using an angled bend 140, the second end 110 of the stylet 104 may be made flexible by choosing the material properties of the stylet 104 to be more flexible proximal to the second end 110 compared to the remainder of the stylet 104. Alternatively, a pivot means such as a ball joint may be connected to the second end 110 to rotatably connect the stylet 104 and the module 106. In this case, there would be a hole to allow for the passage of the optical fibers between the shaft 104 and the module 106.

In use, the video scopes 40 and 100 will behave in substantially the same manner and so the use of the video scope 40 will only be discussed. Once the video scope 40 is inserted into the endotracheal tube 10, the medical practitioner who is performing the intubation shapes the endotracheal tube 10 into a desired configuration according to the patient who is being intubated. This may range from a straight shape, to a gentle curve to an L-shape. The video scope 40 is then activated by pressing the power button 58. The endotracheal tube 10 is held in the medical practitioner's hand and under direct line of sight, by viewing the image 142 on the monitor 56, the tip 12 of the endotracheal tube 10 is placed into the posterior oropharynyx (i.e. the back of the mouth) of the patient. The image 142, showing the patient's vocal cords and glottis, is used by the medical practitioner to direct the tip 12 of the endotracheal tube 10 towards the opening of the patient's trachea. The endotracheal tube 10 is then placed between the vocal cords and introduced into the trachea at the proper location. The proper location is found either by direct visualization of the bronchi and carina (i.e. the first bifurcation of the trachea) or by using predetermined norms for endotracheal position and listening to the patient's breathing sounds. The video scope 40 is then deactivated by pressing the power button 58. The endotracheal tube 10 is then secured to the patient in the usual fashion after which the stylet 42 is removed.

Alternatively, during use, the medical practitioner may try to first insert the endotracheal tube 10 without the use of the video scope 40. If the medical practitioner encounters problems and suspects a difficult airway, the medical practitioner may then insert the stylet 42 into the endotracheal tube 10 as previously described and carry out the procedure outlined in the preceding paragraph.

In a further alternative, during use, the medical practitioner may insert the stylet 42 such that the tip 48 of the stylet 42 extends 1 to 2 cm past the tip 12 of the endotracheal tube 10. This would then allow the medical practitioner to place the tip 48 of the stylet 42 between the vocal cords of the patient. Next, the endotracheal tube 10 may be advanced beyond the tip 46 of the stylet 42. Once in place, the endotracheal tube 10 is secured to the patient in the usual fashion and the stylet 42 is removed. This alternative technique may be advantageous in situations where the patient's trachea presents little room for positioning the larger diameter endotracheal tube 10 into the trachea.

It should be understood that various modifications can be made to the preferred embodiments described and illustrated herein without departing from the present invention. For instance, the video scope 40 (100) of the subject invention may also be used for other medical purposes such as preoperative airway assessment and assistance in looking for foreign bodies in the upper airway. The video scope 40 (100) of the present invention may also be used with a conventional laryngoscope. The video scope 40 (100) may also be used to provide an image of several cavities within the human body or any animal body of which the esophagus and the trachea are only two examples.

What is claimed is:

1. A vision system for use with an endotracheal tube for obtaining an image of an inner cavity of a patient, said vision system comprising:
   a) a stylet having a first end, a second end and a flexible shaft disposed therebetween, said first end being adapted for placement within said cavity during use and said shaft having a lumen;
   b) a module mounted adjacent to said second end of said stylet, said module having a monitor upon which said image is displayed;
   c) an optical system disposed within said module and within said lumen for providing light to illuminate a region proximal to said first end and for obtaining an image of said illuminated region for displaying on said monitor, and;
   d) an adjusting means for adjusting the vertical and horizontal position of said monitor.

2. The vision system of claim 1, wherein the adjusting means includes a rotatable connection.

3. The vision system of claim 1, wherein said vision system further comprises an extension piece, said extension piece being releasably connectable with said second end of said stylet thereby increasing the length of said stylet.

4. The vision system of claim 1, wherein said vision system is for use with an endotracheal tube having a universal adaptor, said vision system further comprising a connector for engaging said universal adaptor, wherein said connector is slidably mounted on said shaft to engage endotracheal tubes of various lengths.

5. The vision system of claim 1, wherein said module is removably attachable to said second end of said stylet.

6. The vision system of claim 1, wherein said optical system comprises:
   i) a light source for providing light to said region;
   ii) a transmission means disposed along said optical system, the transmission means being adapted for transmitting light or an electrical signal representing said image throughout the optical system;
   iii) an objective lens system at said first end of said shaft for receiving reflected light from said region; and,
   iv) a light sensor, in communication with said objective lens system and said monitor, the light sensor receives said reflected light and produces the electrical signal representing said image.

7. The vision system of claim 1, wherein the adjusting means is the flexible shaft.

8. A vision system for obtaining an image of an inner cavity of a patient, said vision system comprising:
   a) a stylet having a first end, a second end and a flexible shaft disposed therebetween, said first end being adapted for placement within said cavity during use and said shaft having a lumen;
   b) a module removably connectable to said second end of said stylet, said module having a monitor upon which said image is displayed;
   c) an optical system disposed within said module and within said lumen for providing light to illuminate a region proximal to said first end and for obtaining an image of said illuminated region for displaying on the monitor; and,
   d) an extension piece releasably connectable with said second end of said stylet, the extension piece being connectable to the second end of the stylet when the module is not connected;

whereby, in use, after the stylet is placed in said inner cavity, the module may be removed and the extension piece may be connected to the stylet thereby increasing the length of said stylet and enabling a medical practitioner to slide an endotracheal tube over the combination of the extension piece and the stylet.

9. The vision system of claim 8, wherein the vision system further includes an adjusting means for adjusting the vertical and horizontal position of said monitor.

10. The vision system of claim 8, wherein said optical system comprises:
   i) a light source for providing light to said region;
   ii) a transmission means disposed along said optical system, the transmission means being adapted for transmitting light or an electrical signal representing said image throughout the optical system;
   iii) an objective lens system at said first end of said shaft for receiving reflected light from said region; and,
   iv) a light sensor, in communication with said objective lens system and said monitor, the light sensor being adapted to receive said reflected light and produce the electrical signal representing said image.

11. The vision system of claim 10, wherein the light sensor includes a camera chip in communication with said objective lens system for receiving said reflected light and for producing an electrical signal, and wherein the optical system provides the electrical signal to said monitor for display thereon.

12. The vision system of claim 8, wherein said vision system is for use with an endotracheal tube having a universal adaptor, said vision system further comprising a connector for engaging said universal adaptor, wherein said connector is slidably mounted on said shaft to engage endotracheal tubes of various lengths.

13. A vision system for obtaining an image of an inner cavity of a patient, said vision system comprising:
   a) a stylet having a first end, a second end and a flexible shaft disposed therebetween, said first end being adapted for placement within said cavity during use and said shaft having a lumen;
   b) a module removably connectable to said second end of said stylet, said module having a monitor upon which said image is displayed;
   c) an optical system disposed within said module and within said lumen for providing light to illuminate a region proximal to said first end and for obtaining an image of said illuminated region for displaying on said monitor, the optical system including a light sensor mounted in said first end, wherein the light sensor produces an electrical signal representing said image; and,
   d) an extension piece releasably connectable with said second end of said stylet, the extension piece being connectable to the second end of the stylet when the module is not connected;
whereby, in use, after the stylet is placed in said inner cavity, the module may be removed and the extension piece may be connected to the stylet thereby increasing the length of said stylet and enabling a medical practitioner to slide an endotracheal tube over the combination of the extension piece and the stylet.

14. The vision system of claim 13, wherein said vision system is for use with an endotracheal tube having a universal adaptor, said vision system further comprising a connector for engaging said universal adaptor, wherein said connector is slidably mounted on said shaft to engage endotracheal tubes of various lengths.

15. The vision system of claim 13, wherein said optical system comprises:
   i) a light source within said module for providing light;
   ii) an illumination channel within said lumen and in communication with said light source for providing said light to said region;
   iii) an objective lens system at said first end of said shaft for receiving reflected light from said region; and,
   iv) a camera chip disposed within the light sensor, the camera chip being in communication with said objective lens system for receiving said reflected light and for producing the electrical signal,
wherein the optical system provides the electrical signal to said monitor for display thereon.

16. The vision system of claim 13, wherein the vision system further includes an adjusting means for adjusting the vertical and horizontal position of said monitor.

17. A two-piece vision system for use with an endotracheal tube for obtaining an image of a patient's throat region, said vision system comprising:
   a) a stylet disposed within said first piece, said stylet having a first end, a second end and a flexible shaft disposed therebetween, said first end being adapted for placement within said throat region during use and said shaft having a lumen;
   b) a first portion of an optical system disposed within said lumen, the first portion of the optical system being adapted to deliver light to illuminate a region proximal to said first end of said stylet and to obtain resulting reflected light representing an image of said illuminated region;
   c) a module disposed in said second piece, said module being releasably mounted near said second end of said stylet; and,
   d) a second portion of the optical system disposed in said module, the second portion of the optical system being in communication with the first portion of the optical system and including a monitor upon which said image is displayed.

18. The vision system of claim 17, wherein the first piece has a longitudinal axis and the second piece is disposed at an angle with respect to the longitudinal axis of the first piece, and the vision system includes an adjusting means for adjusting the orientation of the first piece relative to the second piece.

19. A vision system for use with an endotracheal tube for obtaining an image of an inner cavity of a patient, said vision system comprising:
   a) a stylet having a first end, a second end and a flexible shaft disposed therebetween, said first end being adapted for placement within said cavity during use and said shaft having a lumen;
   b) a module mounted adjacent to said second end of said stylet, said module having a monitor upon which said image is displayed; and,
   c) an optical system disposed within said module and within said lumen for providing light to illuminate a region proximal to said first end and for obtaining an image of said illuminated region for displaying on said monitor, wherein the module is rotatably connected to the shaft adjacent said second end to enable adjustment of the vertical and horizontal position of said monitor.

* * * * *